United States Patent
Li

(10) Patent No.: US 12,322,500 B1
(45) Date of Patent: Jun. 3, 2025

(54) PREDICTING SURGICAL CASE LENGTHS USING MACHINE LEARNING

(71) Applicant: LeanTaaS, Inc., Santa Clara, CA (US)

(72) Inventor: Zetong Li, Sunnyvale, CA (US)

(73) Assignee: LeanTaaS, Inc., Santa Clara, CA (US)

( * ) Notice: Subject to any disclaimer, the term of this patent is extended or adjusted under 35 U.S.C. 154(b) by 965 days.

(21) Appl. No.: 17/402,154

(22) Filed: Aug. 13, 2021

Related U.S. Application Data

(60) Provisional application No. 63/069,897, filed on Aug. 25, 2020.

(51) Int. Cl.
*G16H 40/20* (2018.01)
*G06N 20/00* (2019.01)

(52) U.S. Cl.
CPC ............ *G16H 40/20* (2018.01); *G06N 20/00* (2019.01)

(58) Field of Classification Search
CPC .............................. G16H 40/20; G06N 20/00
USPC .......................................................... 706/12
See application file for complete search history.

(56) References Cited

U.S. PATENT DOCUMENTS

| | | | |
|---|---|---|---|
| 10,924,348 B1* | 2/2021 | Yu | H04L 41/0636 |
| 2016/0140858 A1* | 5/2016 | Adderly | G06F 40/30 |
| | | | 704/9 |
| 2018/0349557 A1* | 12/2018 | Li | G16H 80/00 |
| 2020/0012673 A1* | 1/2020 | Rudzicz | G06F 16/242 |

OTHER PUBLICATIONS

Machine Learning Approach to Predicting Case Duration for Robot-Assisted Surgery by Zhao et al, 2019 (Year: 2019).*

* cited by examiner

*Primary Examiner* — Austin Hicks
(74) *Attorney, Agent, or Firm* — Sheppard Mullin Richter & Hampton LLP

(57) ABSTRACT

The prediction system accesses a flowchart of questions relating to surgical cases and receives, for each of set of surgical case identifiers, surgical case information and an actual surgical case length. The prediction system trains a machine learning model to predict surgical case lengths using the surgical case information and prunes the flowchart by removing questions associated with a uniform set of answers. The prediction system receives, from a client device, a request to reserve an operating room for a surgical case, and transmits, for display via a user interface of the client device, questions from the flowchart. The prediction system receives a feature vector of answers to the transmitted questions from the client device and inputs a type surgical case and the feature vector to the machine learning model, which outputs a predicted surgical case length. The prediction system reserves an operating room for the predicted surgical case length.

17 Claims, 8 Drawing Sheets

PREDICTING SURGICAL CASE LENGTHS USING MACHINE LEARNING

CROSS REFERENCE TO RELATED APPLICATIONS

This application claims the benefit of U.S. Provisional Application No. 63/069,897, filed Aug. 25, 2020, which is incorporated by reference in its entirety.

BACKGROUND

This invention relates generally to predicting surgical case lengths, and more particularly, to using a question flowchart and a machine learning model to predict surgical case lengths.

Scheduling surgical cases is often a challenging task. Many systems require a medical professional to input a procedure code representing a type of surgical case and information describing resources needed to perform the surgical case. However, such inputs may only generically describe a surgical case, and scheduling a surgical case based on this limited information may result in over- or under-scheduling, leading to waste of time and resources at a medical facility. For example, two patients may each require a knee replacement. Without additional information, a medical professional may assume that a surgery for each patient will take the same amount of time (e.g., 4 hours) and reserve operating rooms accordingly. However, if one patient requires hardware from a previous surgery to be removed during the knee replacement, their surgical case may take longer than 4 hours to perform, and if the other patient only requires a partial knee replacement, rather than a full knee replacement, their surgical case may take shorter than 4 hours to perform. Effectively predicting these differences is difficult without such information.

SUMMARY

A prediction system predicts surgical case lengths to more effectively reserve and utilize operating rooms for complex surgical cases. To predict surgical case lengths, the prediction system uses a machine learning model trained on answers to questions from a flowchart and information describing completed surgical cases.

The prediction system accesses a flowchart of questions to present to a medical professional who is familiar with a surgical case. The prediction system transmits questions to a client device associated with the medical professional based on answers to previous questions. For example, if a medical professional answers "Yes" to the question "Does the operation require revision?" the prediction system may transmit the question "How many levels need to be revised?" whereas, if medical professional answers "No," the prediction system may transmit a different question. By guiding the medical professional through these questions, the prediction system gains more information about the surgical case for input to the machine learning model. Using the answers received, the machine learning model predicts a surgical case length indicating how long an operating room should be reserved for the surgical case and reserves the operating room for the predicted surgical case length. The prediction system stores the answers in relation to the surgical case and uses the stored surgical cases and answers to train the machine learning model. In some embodiments, the prediction system may also receive actual time that a surgical case took to perform and store the actual time with the surgical case, answers, predicted surgical case length, and other information describing the completed surgical case for training the machine learning model.

Furthermore, the prediction system prunes the flowchart to remove questions. The prediction system removes questions yielding a high percentage of the same answer or a low percentage of an answer. For instance, the prediction system may remove the question "Is this an elective procedure?" for plastic surgeries when 100% of the answers from medical professionals are "Yes" out of the answers "Yes" and "No." The prediction system may continuously prune the flowchart upon receiving answers for various surgical cases.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

The figures depict embodiments of the present invention for purposes of illustration only. One skilled in the art will readily recognize from the following description that alternative embodiments of the structures and methods illustrated herein may be employed without departing from the principles of the invention described herein.

DETAILED DESCRIPTION

Overview

Figure 1:
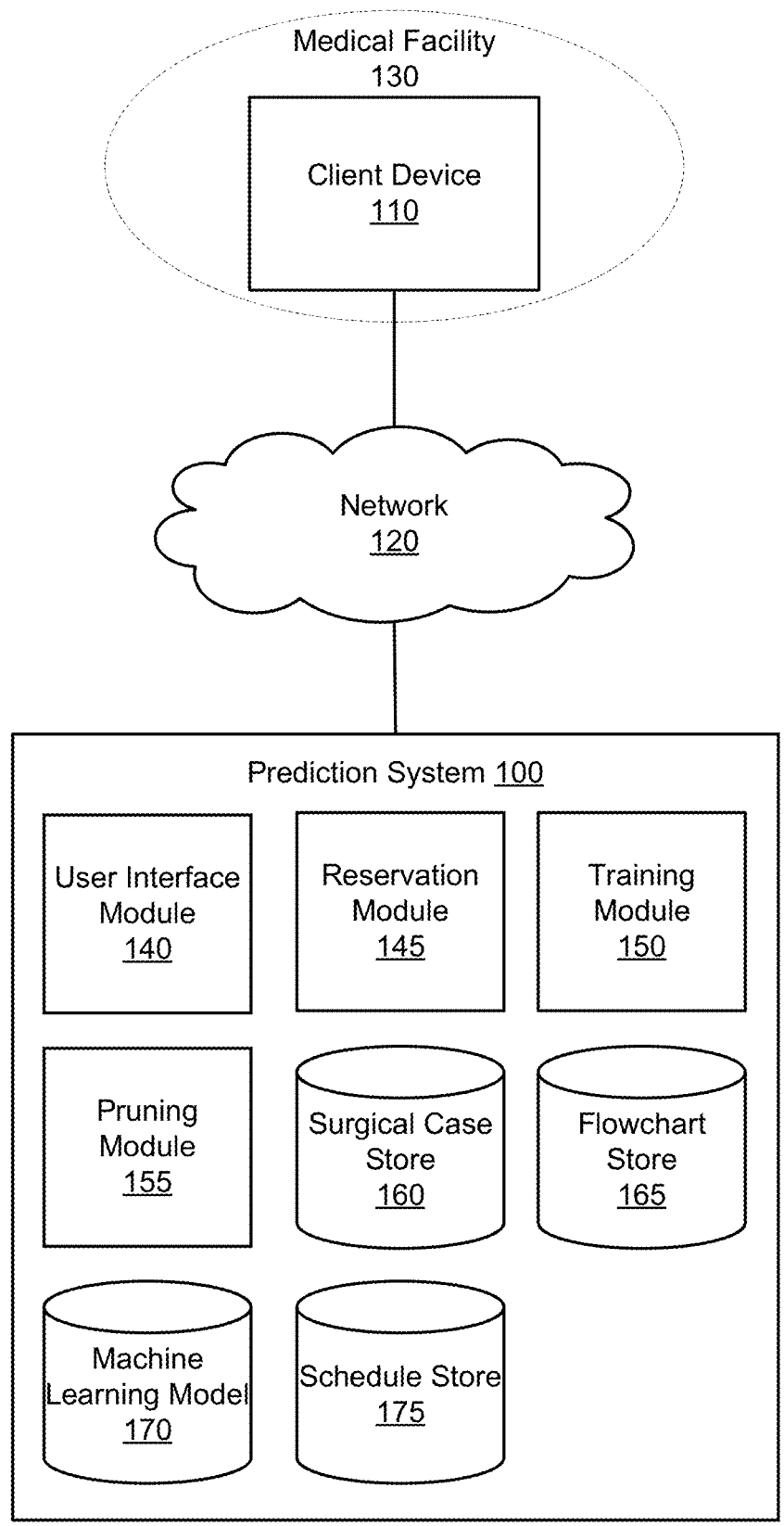
FIG. 1 illustrates a computing environment for a prediction system, according to one embodiment.

FIG. 1 illustrates a computing environment for a prediction system 100, according to one embodiment. The computing environment includes the prediction system 100, a client device 110, and a network 120. Though only one client device 110 is shown in FIG. 1, other embodiments may use more than one client device. These various components are now described in additional detail.

The client device 110 is a computing device such as a smart phone, laptop computer, desktop computer, or any other device that can access the schedule generation system 100. In some embodiments, the client device 110 provides a number of third-party applications access to the prediction system 100 via the network 120. The client device may be located in a medical facility 130 for medical professionals to access. The client device may depict one or more questions with answer choices for a medical professional to choose from and may output a predicted surgical case length or a confirmation of a reservation of an operating room for the predicted surgical case length, as described in relation to the prediction system 100 below.

The network 120 may be any suitable communications network for data transmission. In an embodiment such as that illustrated in FIG. 1, the network 120 uses communications technologies and/or protocols and can include the Internet. In another embodiment, the entities use custom and/or dedicated data communications technologies. The network 120 connects the client device 110 (or client devices, in other embodiments) to the prediction 100 such that the client device 110 and prediction system 100 can transmit data back and forth.

The prediction system 100 predicts a surgical case length, using a machine learning model, given a set of answers to questions that relay information about a surgical case. A surgical case is a medical operation to be performed on a patient by a medical professional. Examples of surgical cases include arthroscopies, biopsies, bypasses, or any other operative medical procedure. A surgical case may be represented by a generic name (e.g., "Mastectomy") or procedure code (e.g., "294-0316" for a mastectomy) but may involve nuances related to the operative procedure itself or the patient not indicated by the generic name or procedure code. For example, though two patients may each be scheduled to undergo mastectomies, one patient may require a partial mastectomy, while the other patient may require a double mastectomy. In another example, of two people who will receive knee arthroplasties (i.e., knee replacements), one may need extra hardware removal from a previous knee arthroplasty, while the other may not. These generic names and standard medical codes do not distinguish between different types of procedures (e.g., partial mastectomy or double mastectomy) or provide context for effectively determining differences in surgical cases (e.g., needing hardware removal or not).

In another example, two people may each require anterior lumbar fusion. However, each person may have a different number of levels that need to be worked on and a different number of levels impacted. By referring to surgical cases for anterior lumbar fusion by a generic name or standard medical code information further describing the intricacies of each surgical case (e.g., the different levels that need work or are impacted) may not be evident to the prediction system 100 for determining surgical case lengths for each person's surgical case.

The prediction system 100 transmits questions from a question flowchart for a medical professional to answer to determine these details about the surgical case. The prediction system 100 receives answers to the questions and inputs the answers to a machine learning model. The machine learning model is trained to predict a surgical case length for a surgical case using answers to questions from the question flowchart. The prediction system 100 updates the flowchart based on answers retrieved for multiple surgical cases, such that the question flowchart focuses on questions that yield answers that help the machine learning model determine surgical case lengths.

The prediction system 100 includes a user interface module 140, a reservation module 145, a training module 150, a pruning module 155, a surgical case store 160, a flowchart store 165, a machine learning model 170, and a schedule store 175. In some embodiments, the prediction system 100 has more or different components than those shown in FIG. 1. In other embodiments, the components shown in FIG. 1 may be combined or removed.

The user interface module 140 transmits a user interface to one or more client devices 110 connected to the prediction system 100 via the network 120, and one or more medical professionals may interact with the user interface via the one or more client devices 110. The user interface module 140 retrieves a schedule for one or more operating rooms at a medical facility 130 from the schedule store 175 and depicts the schedule in the user interface. For example, user interface may depict available and reserved blocks of time for each operating room.

The user interface module 140 receives, from a client device 110, a request to reserve an operating room for a surgical case. A request indicates a medical professional's desire to reserve an operating room for a surgical case and includes a surgical type identifier, which may be a generic name or a procedure code indicating a type of surgical case, and a patient identifier, such as the name of a patient undergoing the surgical case. For example, the request may include the surgical type identifier "ACL reconstruction" and the patient identifier "Larry Lyon." The request also includes a name of a medical facility 130 and a name of the medical professional who will perform the surgical case and may further include identifiers of one or more operating rooms at the medical facility 130 and descriptive information describing the surgical case. The descriptive information may describe conditions specific to a patient, resources needed to perform the surgical case, or any other information related to the surgical case. The user interface module 140 assigns the request a surgical case identifier, which may be used to identify the surgical case of the request and stores the request in relation to surgical case identifier in the surgical case store 160.

Upon receiving the request, the user interface module 140 accesses the flowchart store 165. The flowchart store 165 stores a flowchart of questions, herein referred to as a question flowchart, connected to one another with answers. In some embodiments, the flowchart store 165 may store a question flowchart for each name or procedure code of a surgical case. For example, for the surgical case "Rhinoplasty," the question "Is this operation elective?" is associated with the answers "Yes" and "No." The answer "Yes" is further related to the question "What type of rhinoplasty is this?" while the answer "No" is further related to the question "Does the patient have a deviated septum?". The structure of the question flowchart and answers in the flowchart store 165 is further described in relation to FIG. 2.

The user interface module 140 retrieves a question from the flowchart store 165. In some embodiments, the user interface module 140 retrieves a question related to the surgical type identifier associated with the request. In other embodiments, the user interface module 140 retrieves a starting question from the flowchart store 165, which is the first question in the question flowchart that leads to other questions requesting more specific information about the surgical case. For example, the starting question may ask for the name of the surgical case if not included with the request. The user interface module 140 also retrieves a set of answers associated with the question from the flowchart store 165.

The user interface module 140 transmits a user interface including the question and set of answers. The set of answers are associated with interactive elements in the user interface that allow a medical professional interacting to select an answer via the client device 110. The user interface module 140 may transmit the answers to be displayed in an order, such as from most to least often selected. In some embodiments, the user interface may further include a text field for receiving an answer not included in the set of answers. The user interface module 140 receives an answer from the client device 110 and stores the answer in the surgical case store 150 in relation to the surgical case identifier of the request. In some embodiments, the user interface module 140 also stores the question in the surgical case store 150 with the answer. Based on the answer, the user interface module 140 retrieves a next question associated with the answer and a next set of answers associated with the next question from the flowchart store 165. In some embodiments, the user interface module 140 may receive multiple answers for a question and retrieves a question associated with each answer from the flowchart store 165.

The user interface module 140 iterates upon transmitting the user interface with a new question and a new set of answers to the client device 110 and storing the answer in relation to the surgical case identifier in the surgical case store 160 until it reaches an ending answer of the flowchart store 165. An ending answer is not associated with any further related questions in the question flowchart. The user interface module 140 receives an ending answer from the client device 110, which it stores in the surgical case store 150 in association with the surgical case identifier. In some embodiments, upon receiving an ending answer, the user interface module 140 transmits a question asking the user to confirm a descriptor of the surgical case based on the answers received. For instance, the user interface module 140 may transmit the question "Is this operation a L4-L5 anterior lumbar fusion with a graft?" and the answers "Yes" and "No," which the user may select from. If the user selects "Yes," then the user interface module 140 may stop transmitting questions from the flowchart, and if the user selects "No," then the user interface module 140 may transmit more questions from the flowchart receive more information describing the surgical case.

The user interface module 140 sends the surgical case identifier, surgical type identifier, a feature vector of metadata from the request for the reservation including, but not limited to, identifiers of the patient, surgeon, staff, procedure, implants, and supplies, and also a feature vector of the received answers to the reservation module 145. Alternatively, the user interface module 140 sends the surgical case identifier to the reservation module 145 to indicate that questions from the question flowchart have been answered by a medical professional and the feature vector of answers and surgical type identifier are stored in the surgical case store 160.

In some embodiments, the user interface module 140 receives blocks of time in the schedule from the reservation module and displays the blocks of time in the user interface for a medical professional to select from for scheduling the surgical case. The user interface module 140 receives a selection of a block of time and sends the block of time to the reservation module 145. This process is further described below in relation to the reservation module 145. Furthermore, in some embodiments, the user interface module 140 receives a block of time reserved for the surgical case identifier from the reservation module 145 and transmits a confirmation of the reservation to the client device 110 for display via the user interface. The user interface module 140 may, in some embodiments, transmit, via the user interface, a request for an actual surgical case length for a surgical case after the block of time reserved for surgical case has passed. An actual surgical case length is the amount of time a surgical case took to perform. The user interface module 140 stores the actual surgical case length in relation to a surgical case identifier of the surgical case in the surgical case store 160.

The reservation module 145 reserves an operating room based on a predicted surgical case length. A predicted surgical case length is an estimated amount of time needed to perform the surgical case in an operating room. The reservation module 145 receives a surgical case identifier, a surgical type identifier, a feature vector of answers from the user interface module 140, the name of the medical professional who will perform the surgical case, and the name of the medical facility 130. In alternate embodiments, the reservation module 145 receives the surgical case identifier from the user interface module 140 and retrieves answers and a surgical type identifier associated with the surgical case identifier from the surgical case store 160. The reservation module 145 inputs the surgical type identifier, the feature vector of answers, name of the medical professional, and name of the medical facility 130 to the machine learning model 170. The machine learning model 170 may be a convolutional neural network, a linear regression model, a decision tree, a random forest classifier, or the like. The machine learning model 170 is trained by the training module 150, which is further described below. In some embodiments, the prediction system 100 may use multiple machine learning models 170 each trained for a specific medical facility, medical professional, or surgical type identifier. In some embodiments, the machine learning models 170 may be trained for multiple medical facilities 130, medical professionals who perform surgical cases, and/or surgical type identifiers. The reservation module 145 receives a predicted surgical case length from the machine learning model 170 and stores the predicted surgical case length in the surgical case store in association with the surgical case identifier.

The reservation module 145 retrieves a schedule for one or more operating rooms indicated in the request from the schedule store 175. The reservation module 145 determines available blocks of time in the schedule corresponding to the predicted surgical case length. An available block of time is a segment of time that an operating room at a medical facility 130 is free for reservation. The reservation module 145 selects a block of time corresponding to the predicted surgical case length. In some embodiments, the reservation module 145 may further select a block of time based on an identifier of one or more operating rooms included in the request, a description of the resources need for the surgical case, or a schedule of the medical professional who will perform the surgical case. In other embodiments, if two or more blocks of time of at least the predicted surgical case length are available, the reservation module 145 sends the two or more blocks of time to the user interface module 140, which transmits a user interface to the client device 110 indicating available blocks of time and sends a selected block of time to the reservation module 145. The reservation module 145 updates the schedule in the schedule store 175 to indicate that the selected block of time is reserved for the surgical case of the surgical case identifier and may transmit the selected block of time to the user interface module 140 to display a confirmation of the reservation.

The training module 150 trains the machine learning model 170 to determine surgical case lengths based on answers to questions from the flowchart store 165. The training module 150 determines a set of surgical case identifiers of completed surgical cases in the surgical case store 160. A completed surgical case has been performed in an operating room and is associated with an actual surgical case length indicating how long the surgical case took to perform. For each completed surgical case, the training module 150 retrieves an actual surgical case length and a set of surgical case information from the surgical case store 160. Each set of surgical case information includes a surgical type identifier and feature vector of answers to questions from the flowchart store 165. In some embodiments, the surgical case information also includes questions associated with each answer and/or descriptive information describing resources needed for the surgical case or conditions of the patient undergoing the surgical case. Further, the training module may retrieve answers to all possible questions from the flowchart store 165 and use the answers as input to the machine learning model 170 for training.

The training module 150 labels each set of surgical case information with its corresponding actual surgical case length and uses the labelled sets of surgical case information to train the machine learning model 170. The training module 150 inputs the training data of surgical case information to the machine learning model 170 for training. In some embodiments, the training module 150 trains the machine learning model 170 for a particular medical facility, medical professional, or surgical type identifier by inputting surgical information associated with the medical facility, medical professional, or surgical type identifier to the machine learning model 170.

The pruning module 155 prunes questions and answers from the flowchart store 165. By pruning the flowchart store 165, the questions sent via the user interface module 150 to medical professionals may be more focused on the most relevant information needed about a surgical case for the machine learning model 170 to effectively predict a surgical case length. The pruning module retrieves answers stored in the surgical case store 160 and determines a selection count for each answer indicating how often that answer was selected for different surgical case identifiers, which represent surgical cases, stored in the surgical case store 160. The pruning module accesses the question flowchart in the flowchart store 165 and determines a selection percentage for each answer based on its associated question. For example, the answer "Yes" may have been chosen for the question "Is this procedure elective?" for 28% of surgical cases stored in the surgical case store, while the answer "No" maybe have been chosen for 72% of the surgical cases. The pruning module stores the selection counts and selection percentages in relation to each answer in the flowchart store 165. In some embodiments, the pruning module 155 may update the selection percentages as answers for new surgical case identifiers are stored in the surgical case store 160.

The pruning module 155 removes answers from the question flowchart based on selection percentages and selection counts. For each question in the question flowchart, the pruning module determines a total selection count representative of how many times the question was answered. For instance, the pruning module 155 may determine the total selection count by summing the selection counts of the answers to the question. For each answer, if the associated question has a total selection count above a count threshold and the answer has a selection percentage of 0%, the pruning module 155 removes the answer from the flowchart store 165. For example, for a count threshold of 200, the pruning module 155 would remove an answer with a 0% selection percentage and associated with a question with a total selection count of 306, but would not remove an answer with a 0% selection percentage and associated with a question with a total selection count of 49. This process is illustrated in relation to FIG. 2. In some embodiments, the pruning module 155 may remove answers with a selection percentage below a lower threshold percentage. Further, the pruning module 155 may sort the answers to each question in the flowchart by selection count, such that the user interface module 140 retrieves the answers to the question in order for most to least selected, such that the user interface module 140 may transmit the answers in the order for display on the user interface.

The pruning module 155 also removes questions from the question flowchart with a uniform set of answers. A question has a uniform set of answers if one answer to the question has a selection percentage of 100%. In some embodiments, the pruning module 15 removes answers with a selection percentage above an upper threshold percentage (e.g., 99.9%). The pruning module 155 determines which questions in the flowchart have a total selection count above the threshold count and an answer with a selection percentage of 100% and removes the questions from the flowchart store 165. For example, though a question may have multiple answers, if the question has a total selection count above the threshold count and one of the answers have a selection percentage of 100%, the pruning module 155 removes the question and the answers from the question flowchart in the flowchart store 165.

The pruning module 155 combines answers in the question flowchart. The pruning module 155 retrieves surgical case identifiers for completed surgical cases with actual surgical case lengths and features vectors of answers from the surgical case store 160. For each feature vector of answers of the completed surgical cases, the pruning module 155 determines an estimated time based on the actual surgical case lengths associated with the surgical case. An estimated time represents how long surgical cases associated with the feature vector have taken to complete and, in some embodiments, may be an average of the actual surgical case lengths of completed surgical cases associated with the same feature vector. Estimated times may be in any suitable measurement of time, such as minutes. The pruning module 155 stores the estimated time for each feature vector in the flowchart store 165 along with the feature vector and may update the estimated times as actual case lengths are added to the surgical case store 160.

The pruning module 155 may also remove questions from the question flowchart based on an effect of answers on estimated times of feature vectors. For instance, for each answer stored in the flowchart store 165, the pruning module determines whether the estimated times of the feature vectors with the answer change by more than a threshold amount if the answer changes. If not, the pruning module 155 may remove the question associated with the answer, along with its related answers, from the flowchart store 165. For example, if a question is associated with 3 different answers, and changing the answer to the question in feature vectors including an answer to the question does not change the estimated time by more than 5 minutes (e.g., the threshold amount), the pruning module 155 removes the answer from the flowchart store 165. In some embodiments, the pruning module 155 may use principal component analysis to compare the effect of changing an answer to estimated times of feature vectors.

Further, the pruning module 155 may combine answers that have the same effect (e.g., estimated times within a threshold amount of one another) on feature vectors relative to alternate answers to the same question. For example, for a question with three answers, feature vectors with the first two answers may have estimated times of 90 and 91 minutes, respectively, and feature vectors with the third answer have an estimated time of 72 minutes. In this example, the estimated times for the feature vectors with the first two answers have a time change of 1 minute between them, which is less than a threshold amount of 5 minutes. Thus, the pruning module may combine the first two answers in the flowchart store 165. This process is illustrated in relation to FIG. 2.

Question Flowchart Examples

Figure 2A:
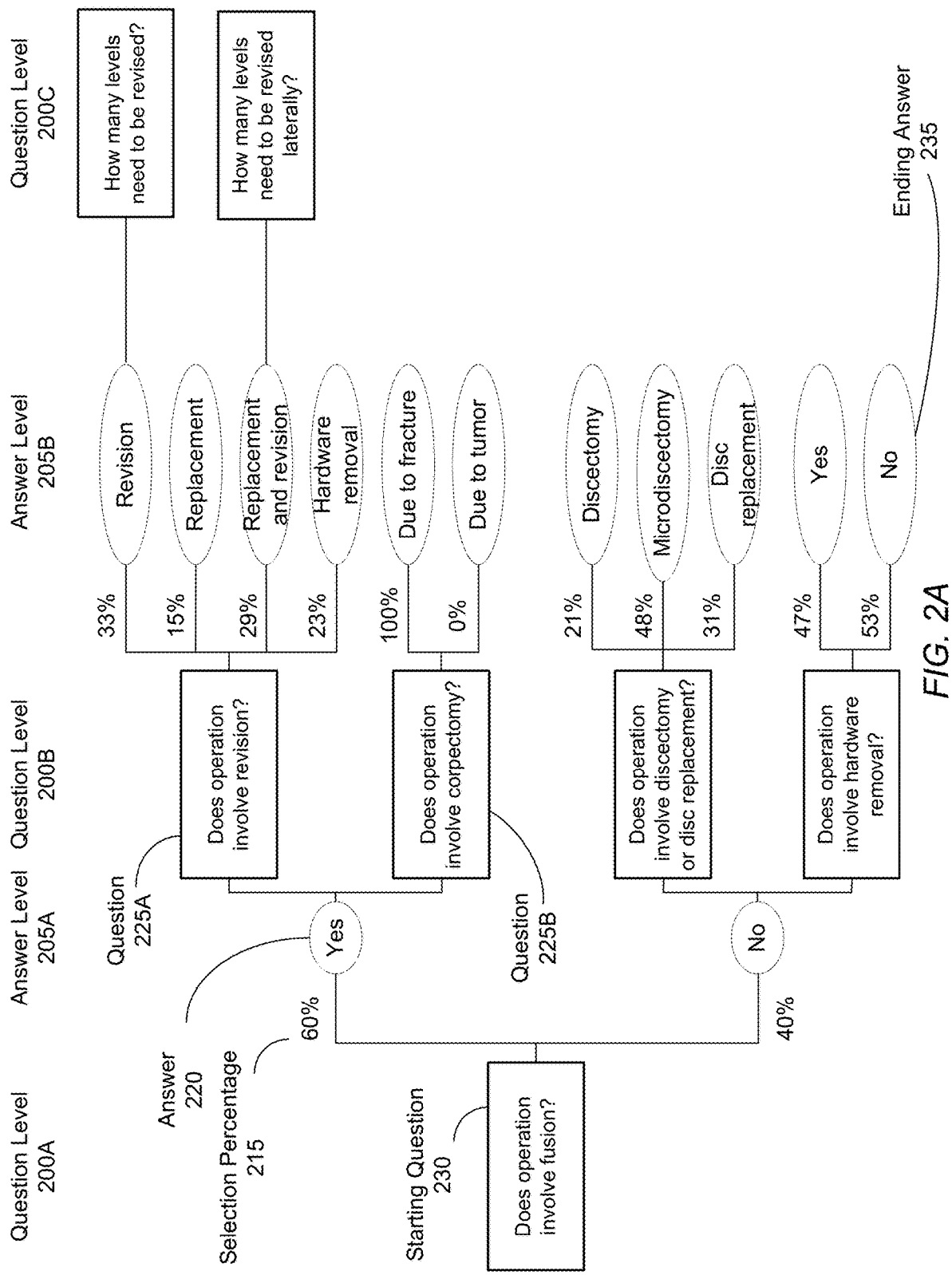
FIG. 2A is illustrates a portion of a question flowchart used by the prediction system, according to one embodiment.

FIG. 2A is illustrates a portion of a question flowchart used by the prediction system 100, according to one embodiment. The question flowchart includes questions 225 and answers 220 arranged in a hierarchical structure. This hierarchical structure is shown by the alternating question levels 200 and answer levels 205 in shown in FIG. 2. In some embodiments, the question flowchart may include more question and answer levels than shown in FIG. 2. The question flowchart begins with a starting question 230 that has answers 220 leading to further questions and includes multiple ending answers 235 that are not connected to further questions. For example, as shown in FIG. 2A, the answer 220 "Yes" to the starting question 230 "Does operation involve fusion?" leads to the questions 225 "Does operation involve revision?" and "Does operation involve corpectomy?". Each answer 220 is associated with a selection percentage 215 representing how often medical professionals have selected the answer 220 to the question 225. Returning to the previous example, the answer 220 "Yes" has a selection percentage 215 of 60%, which indicates that the answer 220 has been chosen 60% of the time the starting question 230 has been presented via a user interface. The prediction system 100 may populate the question flowchart with selection percentages 215 based on answers and surgical case lengths stored in the surgical case store 160.

Figure 2B:
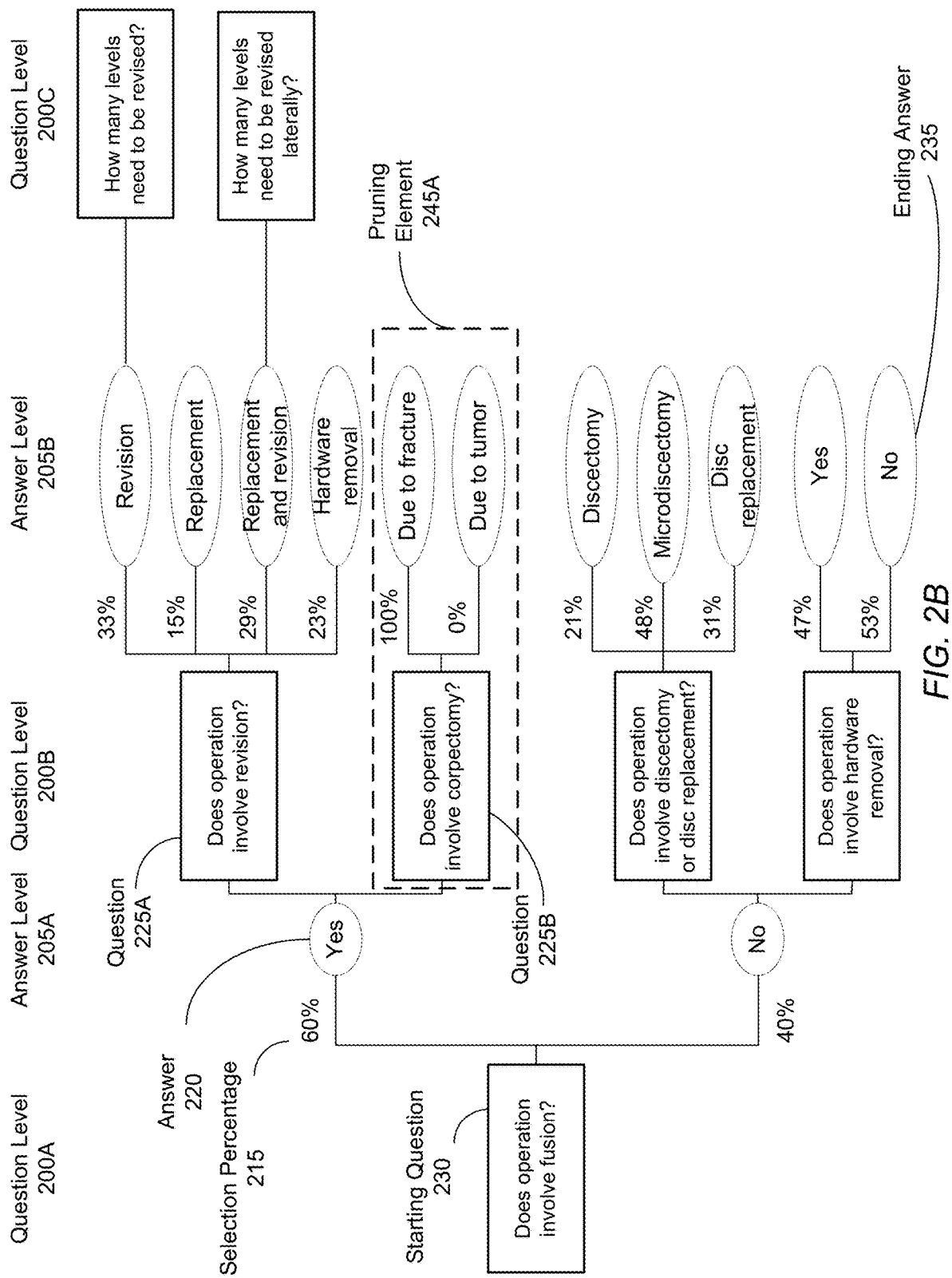
FIG. 2B is illustrates a pruning element in a portion of a question flowchart with a low selection percentage, according to one embodiment.
Figure 2C:
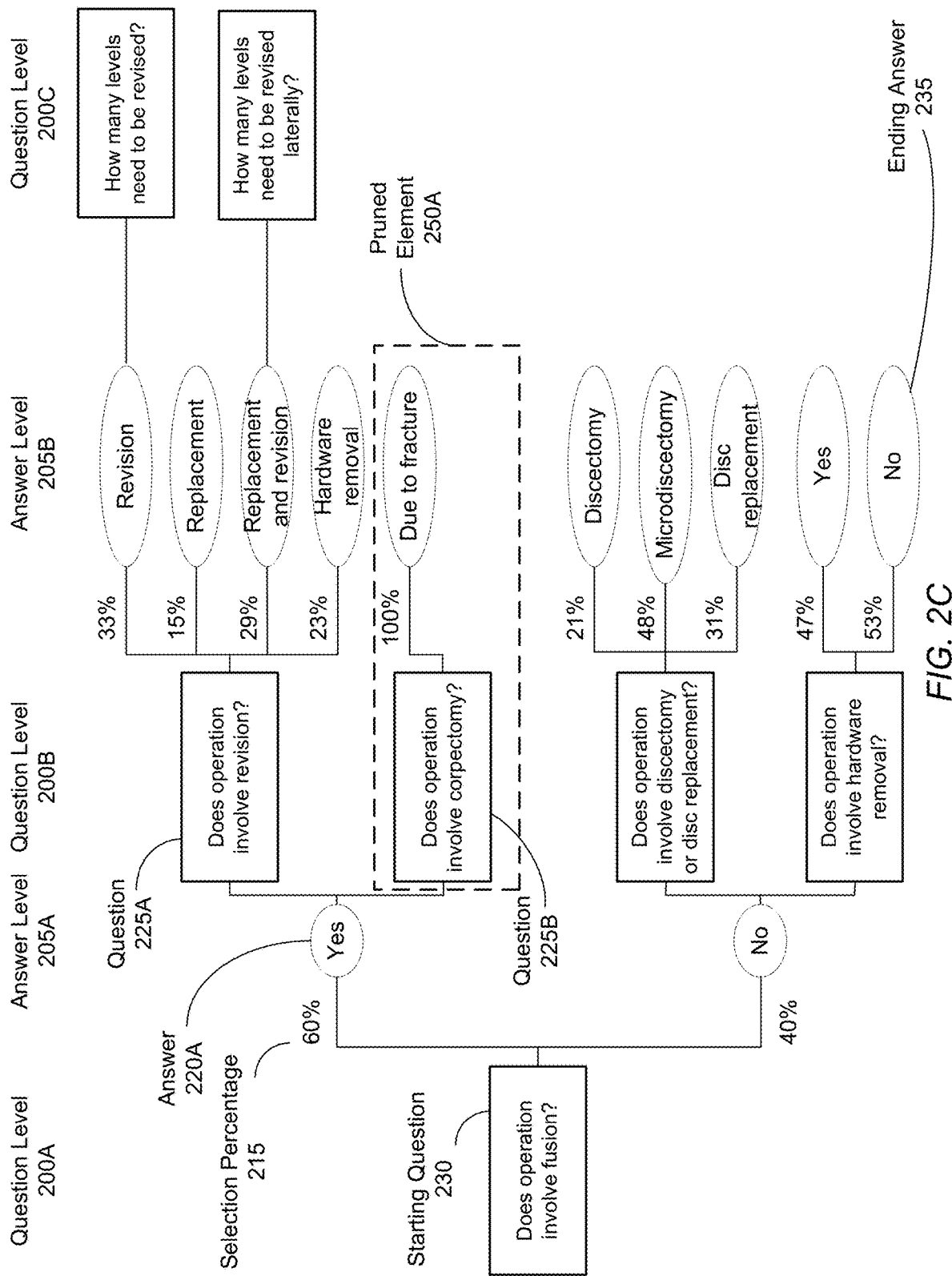
FIG. 2C is illustrates a portion of a question flowchart with an answer removed, according to one embodiment.
Figure 2D:
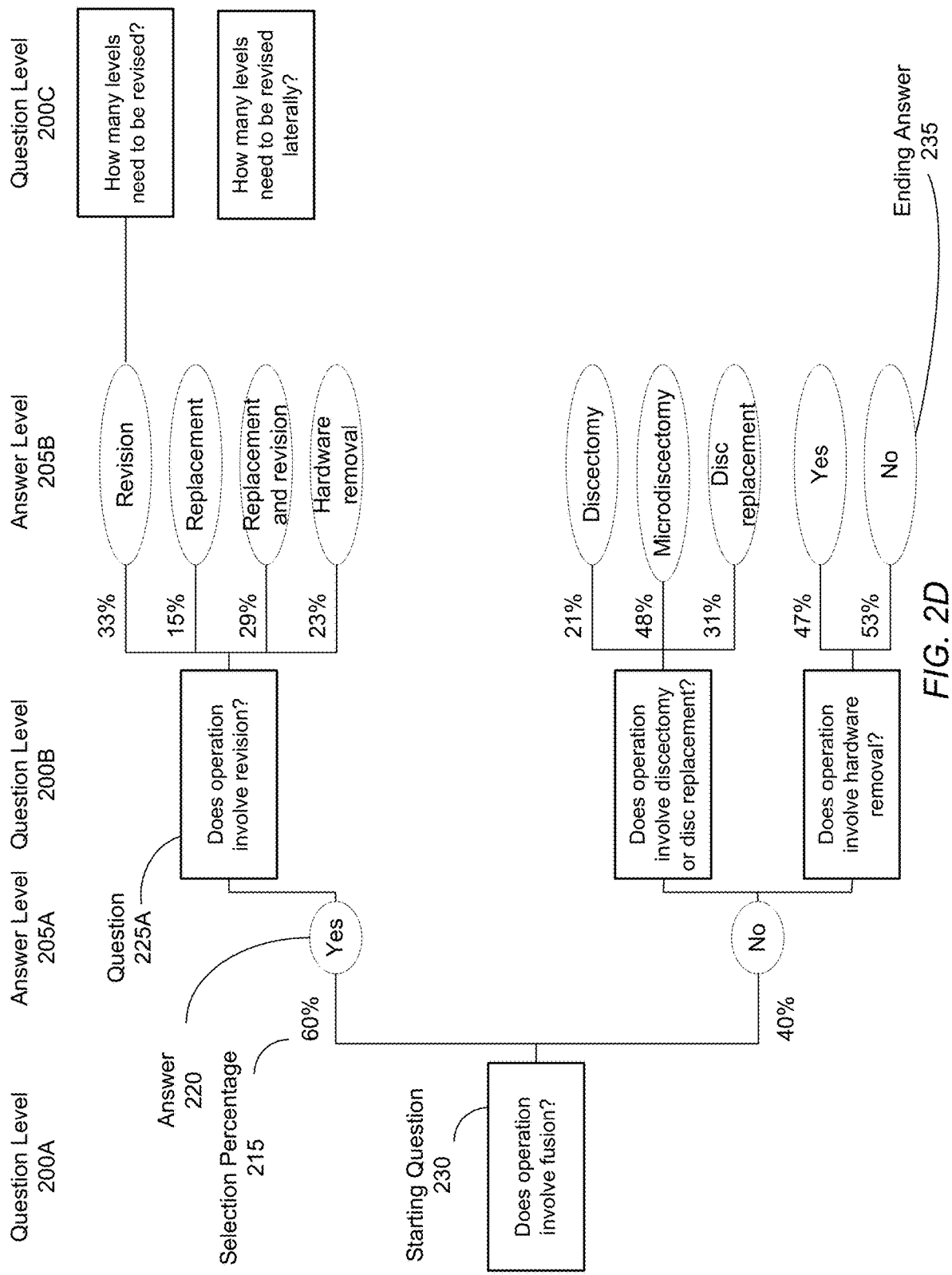
FIG. 2D illustrates a portion of a question flowchart with a question removed, according to one embodiment.

FIG. 2B is illustrates a pruning element 245A in the portion of the question flowchart with a low selection percentage 215, according to one embodiment. A pruning element is a section of the question flowchart that the pruning module 155 will prune. The pruning element 245A of FIG. 2B includes a question 225B with at least one answer 220 that has a selection percentage 215 of 0%. In this embodiment, the question 225B "Does the operation involve corpectomy?" of the pruning element 245A has a total selection count above a threshold count, indicating that the question 225B has been answered at least as many times as the value of the threshold count. Since the total selection count is above the threshold count and the answer 220 "Due to tumor" has a selection percentage 215 of 0%, the pruning module 155 removes the answer 220 "Due to tumor" from the question flowchart, as shown in FIG. 2C. If the question 225B did not have a selection count above the threshold count, then the pruning module 155 would not remove the answer 220, even though it has a selection percentage 215 of 0%. The leftover question flowchart includes the pruned element 250A, which is a section of the question flowchart that the pruning module 155 pruned, with the question 225B and the answer 220 "Due to fracture." However, since the question 225A only has one possible answer left (e.g., "Due to fracture), the pruning module 155 removes the question 225B from the question flowchart, as shown in FIG. 2D. The pruning module 155 also removes the answer "Due to fracture."

Figure 2E:
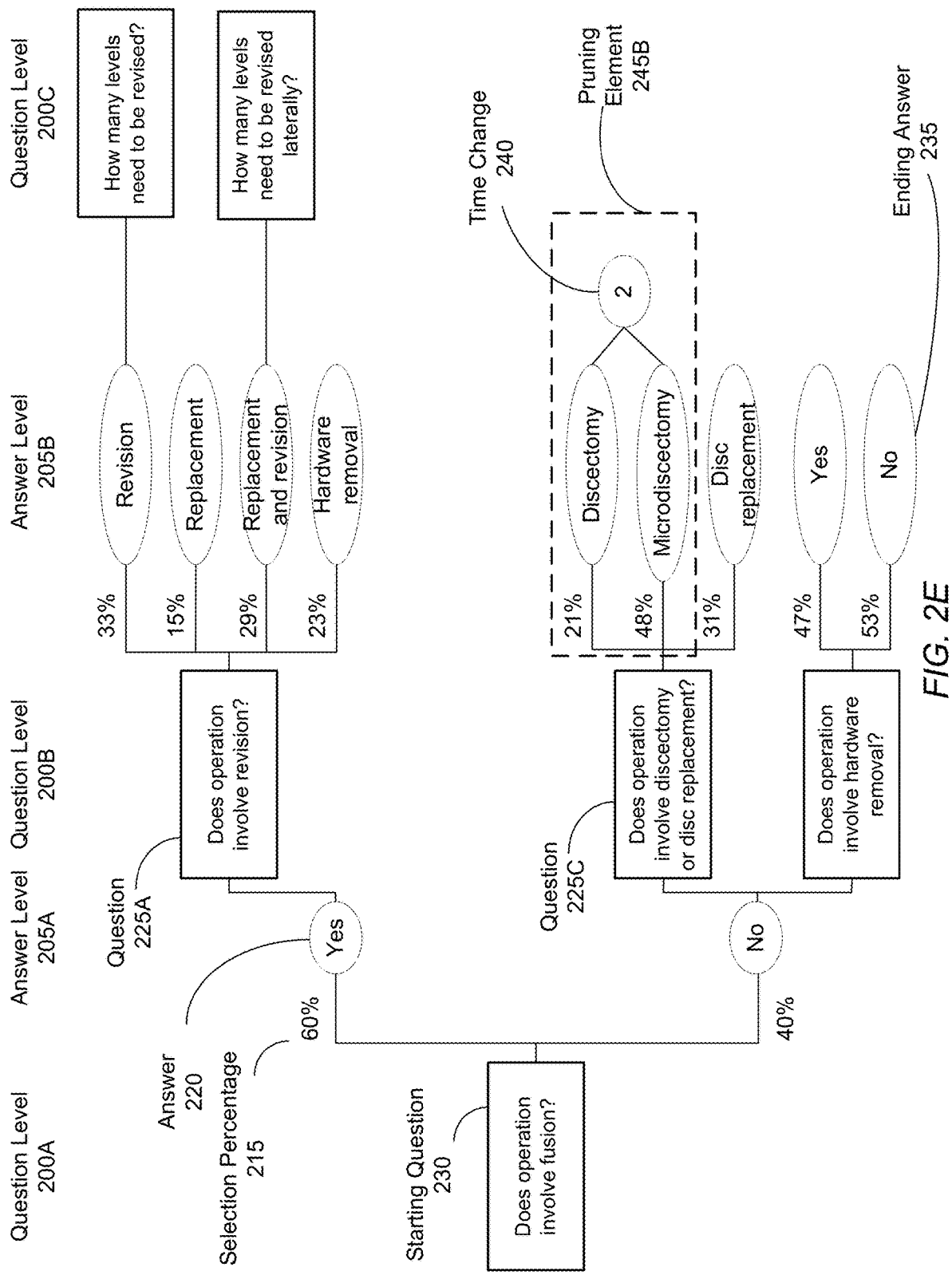
FIG. 2E illustrates a pruning element in a portion of a question flowchart including answers with a low time change, according to one embodiment.
Figure 2F:
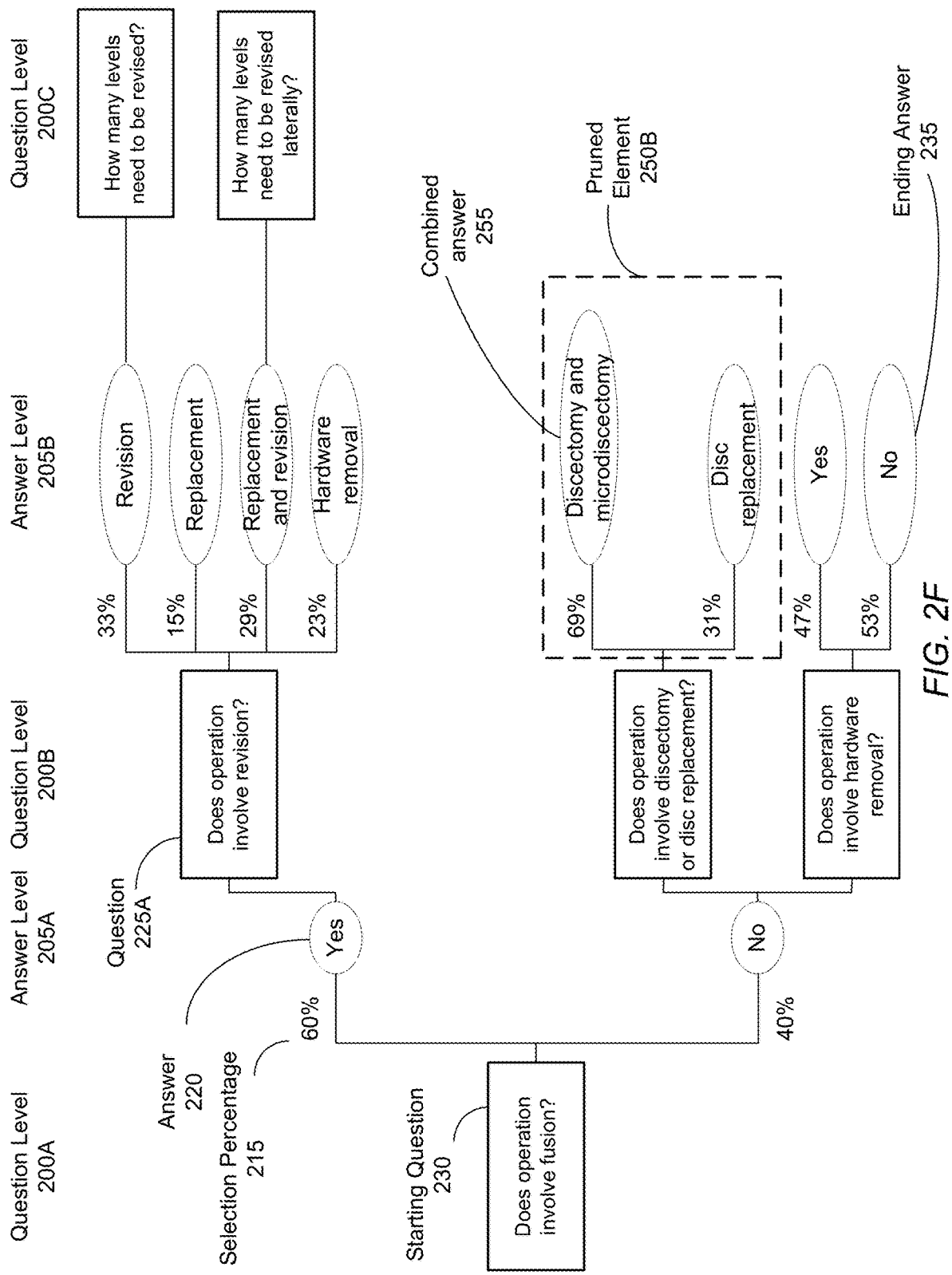
FIG. 2F illustrates a portion of a question flowchart with a combined answer, according to one embodiment.

FIG. 2E illustrates a pruning element 245B in a portion of a question flowchart including answers with a low time change 240, according to one embodiment. A time change 240 is the amount of time that an estimated time of feature vectors with one of the answers 220 to a question 225 changes when the one answer is changed to an alternate answer 220 for the question 225. For example, a first feature vector with the answer 220 "discectomy" to the question 225C "Does operation involve discectomy or disc replacement?" may have an estimated time of 134 minutes, and a second feature vector, with the same answers 220 as the first feature vector other than the answer "microdiscectomy" 220 to the question 225C, may have an estimated time of 132 minutes. Thus, the time change 240 between the two answers 220 is 2 minutes.

The pruning element 245B includes the ending answers 235 "discectomy" and "microdiscectomy," which have a time change of 2 minutes between them. In this embodiment, the pruning module 155 uses a threshold amount of 5 minutes. Since the time change is within the threshold amount, the pruning module 155 combines the answers 220 into the combined answer 255 shown in FIG. 2F. Once the pruning module 155 has pruned the question flowchart, the training module 150 may retrain the machine learning model 170 on surgical case information with questions 225 and answers 220 available from the pruned question flowchart. In other words, the pruning module 155 trains the machine learning model 170 on the surgical case information without questions 225 and answers 220 that were removed from the question flowchart and with combined answers 250 instead of separate answers.

Example Process

Figure 3:
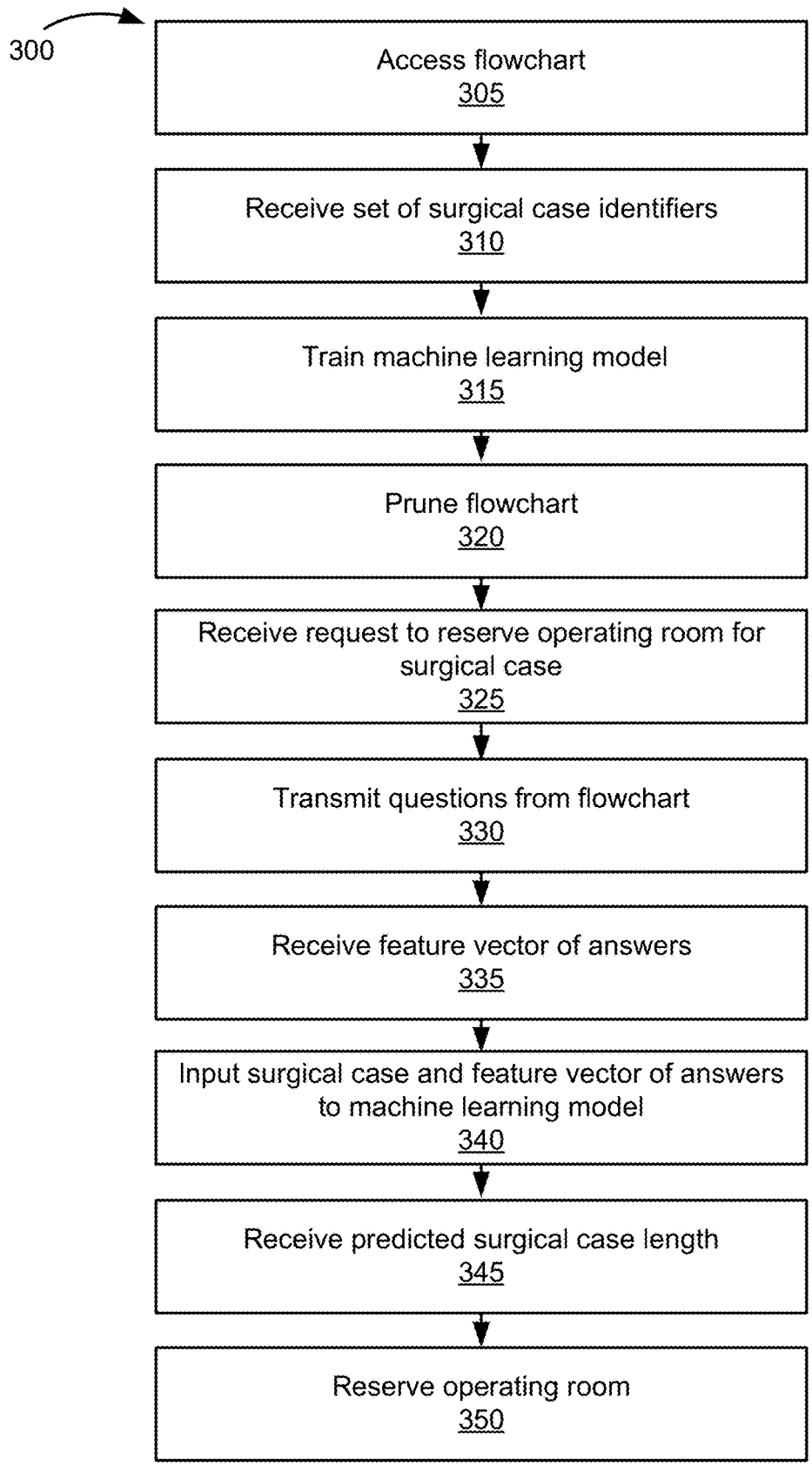
FIG. 3 is a flowchart illustrating the process of reserving an operating room based on a predicted surgical case length, according to one embodiment.

FIG. 3 is a flowchart illustrating the process 300 of reserving an operating room based on a predicted surgical case length, according to one embodiment. The user interface module 140 accesses 305 a question flowchart from the flowchart store 165 and receives 310 a set of surgical case identifiers, each associated with an actual surgical case length and a feature vector of answers 220 to questions 225 from the question flowchart. In some embodiments, the user interface module 140 retrieves, from the flowchart store 165, questions 225 associated with each answer 220 in the feature vector of answers. The training module 150 trains 315 the machine learning model 170 to predict a surgical case length for a surgical case identifier given a feature vector of answers 220. For instance, the training module 150 may label surgical case information, including a feature vector of answers 220, for each surgical case identifier with the actual surgical case length and input the labelled surgical case information into the machine learning model for training.

The pruning module 155 prunes 320 the question flowchart by removing questions 225 associated with a uniform set of answers 220 in the flowchart store 165. For example, the question 225 "Does this operation require hardware removal?" may be associated with the answers 220 "Yes" and "No." However, if the answer 220 "Yes" has a selection percentage 215 of 100%, the pruning module 155 removes the question 225 from the question flowchart.

The user interface module 140 receives 325, via a user interface of a client device 110, a request to reserve an operating room for a surgical case from a client device 100. The request may include surgical type identifier, such as a procedure code or generic name of the surgical case, a patient identifier, and a textual description of the surgical case. In some embodiments, the request may further include a name of the medical professional performing the surgical case, a description of the resources need for the surgical case, a suggested block of time available in the schedule for the operating room, and one or more other operating rooms that may be used in lieu of the requested operating room. The user interface module assigns a surgical case identifier for the request and transmits 330 questions 225 from the question flowchart to the client device 110. Each question is transmitted based on an answer 220 input for the previous question 225. The user interface module 140 receives 335 a feature vector of answers 220 to the questions 225 transmitted from the question flowchart. The reservation module 145 inputs 340 the surgical type identifier and the feature vector of answers to the machine learning model 170 and receives 345, from the machine learning model 170, a predicted surgical case length. The reservation module 145 reserves 350 an operating room for the predicted surgical case length.

Although FIG. 3 illustrates a number of interactions according to one embodiment, the precise interactions and/or order of interactions may vary in different embodiments. For example, in some embodiments, the user interface module 140 transmits a user interface with available blocks of time of at least the predicted surgical case length. The user interface module 149 receives an available block of time from the client device 110, as input via the user interface, and reserves an operating room for the received available block of time.

Other Considerations

The present invention has been described in particular detail with respect to one possible embodiment. Those of skill in the art will appreciate that the invention may be practiced in other embodiments. First, the particular naming of the components and variables, capitalization of terms, the attributes, data structures, or any other programming or structural aspect is not mandatory or significant, and the mechanisms that implement the invention or its features may have different names, formats, or protocols. Also, the particular division of functionality between the various system components described herein is merely for purposes of example, and is not mandatory; functions performed by a single system component may instead be performed by multiple components, and functions performed by multiple components may instead performed by a single component.

Some portions of above description present the features of the present invention in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by real-time network operating systems.

The present invention also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a non-transitory computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of computer-readable storage medium suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, the present invention is not described with reference to any particular programming language. It is appreciated that a variety of programming languages may be used to implement the teachings of the present invention as described herein, and any references to specific languages are provided for invention of enablement and best mode of the present invention.

The present invention is well suited to a wide variety of computer network systems over numerous topologies. Within this field, the configuration and management of large networks comprise storage devices and computers that are communicatively coupled to dissimilar computers and storage devices over a network, such as the Internet.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

What is claimed is:

1. A computer-implemented method for predicting surgical case length, the method comprising:
    accessing a flowchart of questions relating to surgical cases;
    receiving, for each of a set of surgical case identifiers, surgical case information and an actual surgical case length, the surgical case information including a surgical case type and one or more feature vectors of answers to questions from the flowchart;
    training a machine learning model on the surgical case information and on the actual surgical case lengths for the set of surgical case identifiers, the machine learning model trained to predict a future surgical case length for a future surgical case based on a future surgical case type;

pruning the flowchart by removing questions associated with a uniform set of answers;
receiving, via a user interface of a client device, a request to reserve an operating room for a particular future surgical case, the request including a particular future surgical case type;
transmitting, for display via the user interface of the client device, questions from the flowchart, wherein each question is transmitted based on a previous answer input for a previous question;
receiving, from the client device, one or more feature vectors of answers to the questions entered via the user interface;
inputting the particular future surgical case type and the received one or more feature vectors of answers to the questions to the machine learning model;
determining, for each feature vector, an estimated time, the estimated time representing an amount of time surgical cases associated with the feature vector took to perform;
pruning the flowchart based on the estimated times;
receiving, from the machine learning model, a predicted surgical case length for the particular future surgical case; and
reserving the operating room for the predicted surgical case length.

2. The computer-implemented method of claim 1, wherein the flowchart is associated with the particular future surgical case type.

3. The computer-implemented method of claim 1, further comprising:
pruning the flowchart by removing questions with a selection percentage below a lower threshold percentage.

4. The computer-implemented method of claim 1, wherein the machine learning model is trained for a medical professional who will perform the particular future surgical case.

5. The computer-implemented method of claim 1, wherein the machine learning model is trained for the particular future surgical case.

6. The computer-implemented method of claim 1, wherein the machine learning model is trained for a medical facility.

7. The computer-implemented method of claim 1, further comprising:
transmitting, for display via the user interface, a confirmation of the reservation of the operating room, the confirmation including the predicted surgical case length.

8. A non-transitory computer-readable storage medium comprising instructions executable by a processor, the instructions comprising:
instructions for accessing a flowchart of questions relating to surgical cases;
instructions for receiving, for each of a set of surgical case identifiers, surgical case information and an actual surgical case length, the surgical case information including a surgical case type and one or more feature vectors of answers to questions from the flowchart;
instructions for training a machine learning model on the surgical case information and on the actual surgical case lengths for the set of surgical case identifiers, the machine learning model trained to predict a future surgical case length for a future surgical case based on a future surgical case type;
instructions for pruning the flowchart by removing questions associated with a uniform set of answers;
instructions for receiving, via a user interface of a client device, a request to reserve an operating room for a particular future surgical case, the request including a type-f particular future surgical case type;
instructions for transmitting, for display via the user interface of the client device, questions from the flowchart, wherein each question is transmitted based on a previous answer input for a previous question;
instructions for receiving, from the client device, one or more feature vectors of answers to the questions entered via the user interface;
instructions for inputting the type-f particular future surgical case type and the received one or more feature vectors of answers to the questions to the machine learning model;
instructions for determining, for each feature vector, an estimated time, the estimated time representing an amount of time surgical cases associated with the feature vector took to perform;
instructions for pruning the flowchart based on the estimated times;
instructions for receiving, from the machine learning model, a predicted surgical case length for the particular future surgical case; and
instructions for reserving the operating room for the predicted surgical case length.

9. The non-transitory computer-readable storage medium of claim 8, wherein the flowchart is associated with the particular future surgical case type.

10. The non-transitory computer-readable storage medium of claim 8, the instructions further comprising:
instructions for pruning the flowchart by removing questions with a selection percentage below a lower threshold percentage.

11. The non-transitory computer-readable storage medium of claim 8, wherein the machine learning model is trained for a medical professional who will perform the particular future surgical case.

12. The non-transitory computer-readable storage medium of claim 8, wherein the machine learning model is trained for the particular future surgical case.

13. The non-transitory computer-readable storage medium of claim 8, wherein the machine learning model is trained for a medical facility.

14. The non-transitory computer-readable storage medium of claim 8, the instructions further comprising:
instructions for transmitting, for display via the user interface, a confirmation of the reservation of the operating room, the confirmation including the predicted surgical case length.

15. A computer system comprising:
a computer processor; and
a non-transitory computer-readable storage medium storage instructions that when executed by the computer processor perform actions comprising:
accessing a flowchart of questions relating to surgical cases;
receiving, for each of a set of surgical case identifiers, surgical case information and an actual surgical case length, the surgical case information including a surgical case type and one or more feature vectors of answers to questions from the flowchart;
training a machine learning model on the surgical case information and on the actual surgical case lengths for the set of surgical case identifiers, the machine learning model trained to predict a future surgical case length for a future surgical case based on a future surgical case type;

pruning the flowchart by removing questions associated with a uniform set of answers;

receiving, via a user interface of a client device, a request to reserve an operating room for a particular future surgical case, the request including a particular future surgical case type;

transmitting, for display via the user interface of the client device, questions from the flowchart, wherein each question is transmitted based on a previous answer input for a previous question;

receiving, from the client device, one or more feature vectors of answers to the questions entered via the user interface;

inputting the particular future surgical case type and the received one or more feature vectors of answers to the questions to the machine learning model;

determining, for each feature vector, an estimated time, the estimated time representing an amount of time surgical cases associated with the feature vector took to perform;

pruning the flowchart based on the estimated times;

receiving, from the machine learning model, a predicted surgical case length for the particular future surgical case; and reserving the operating room for the predicted surgical case length.

16. The computer system of claim 15, wherein the flowchart is associated with the particular future surgical case type.

17. The computer system of claim 15, the actions further comprising:

instructions for pruning the flowchart by removing questions with a selection percentage below a lower threshold percentage.

* * * * *